United States Patent
Tsuda et al.

(10) Patent No.: US 9,360,569 B2
(45) Date of Patent: Jun. 7, 2016

(54) POSITRON CT APPARATUS AND A TIMING CORRECTION METHOD

(75) Inventors: Tomoaki Tsuda, Kyoto (JP); Masanobu Sato, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 447 days.

(21) Appl. No.: 13/698,971

(22) PCT Filed: May 18, 2010

(86) PCT No.: PCT/JP2010/003340
§ 371 (c)(1),
(2), (4) Date: Nov. 19, 2012

(87) PCT Pub. No.: WO2011/145139
PCT Pub. Date: Nov. 24, 2011

(65) Prior Publication Data
US 2013/0062526 A1    Mar. 14, 2013

(51) Int. Cl.
*G01T 1/20* (2006.01)
*G01T 1/29* (2006.01)
*G01T 1/172* (2006.01)
*G01T 1/164* (2006.01)
*A61B 6/03* (2006.01)

(52) U.S. Cl.
CPC ............... *G01T 1/2985* (2013.01); *A61B 6/037* (2013.01); *G01T 1/1647* (2013.01); *G01T 1/172* (2013.01)

(58) Field of Classification Search
CPC .................... G01T 1/2985; G01T 1/172
See application file for complete search history.

(56) References Cited

U.S. PATENT DOCUMENTS

| | | | | |
|---|---|---|---|---|
| 5,272,344 A * | 12/1993 | Williams | ............... | 250/363.03 |
| 7,709,801 B2 * | 5/2010 | Ooi | ............... | 250/367 |
| 2006/0065825 A1 | 3/2006 | Ishitsu et al. | | |
| 2009/0159804 A1 | 6/2009 | Shibuya et al. | | |

FOREIGN PATENT DOCUMENTS

| JP | 06-019436 B | 3/1994 |
|---|---|---|
| JP | 3343122 | 8/2002 |

(Continued)

OTHER PUBLICATIONS

Translation of Japanese patent No. 6-19436B2 to Seiichi et al.*
(Continued)

*Primary Examiner* — David J Makiya
*Assistant Examiner* — Kenneth J Malkowski
(74) *Attorney, Agent, or Firm* — McDermott Will & Emery LLP

(57) ABSTRACT

A PET apparatus and a timing correction method of this invention select two target gamma-ray detectors which count coincidences, select a reference detector which is one detector out of the two selected gamma-ray detectors, select a gamma-ray detector different from the other, opposite detector, and when repeating the selection, make a time lag histogram concerning two gamma-ray detectors selected in the past a reference, and correct a time lag histogram concerning gamma-ray detectors selected this time based on the reference. By repeating an operation to make the corrected time lag histogram concerning the two gamma-ray detectors a new reference, an optimal time lag histogram can be obtained without repeating many measurements and computations.

8 Claims, 8 Drawing Sheets

(56) References Cited

FOREIGN PATENT DOCUMENTS

| | | |
|---|---|---|
| JP | 2006-090827 A | 4/2006 |
| JP | 2008-051701 A | 3/2008 |

OTHER PUBLICATIONS

International Search Report issued in International Patent Application No. PCT/JP2010/003340 dated Jun. 22, 2010.

* cited by examiner

POSITRON CT APPARATUS AND A TIMING CORRECTION METHOD

RELATED APPLICATIONS

This application is the U.S. National Phase under 35 U.S.C. §371 of International Application No. PCT/JP2010/003340, filed on May 18, 2010, the disclosure of which Application is incorporated by reference herein.

TECHNICAL FIELD

This invention relates to a positron CT apparatus for detecting radiation released from a positron-emitting drug introduced into the body of a patient, and to a timing correction method.

BACKGROUND ART

A positron CT apparatus, i.e. a PET (Positron Emission Tomography) apparatus, is constructed to detect a plurality of gamma rays generated by annihilation of positively charged electrons (positrons), and reconstruct an image of the patient only when a plurality of detectors detect gamma rays at the same time (that is, only when coincidences are counted).

A coincidence counting circuit is used to count coincidences. However, a signal time lag occurs in a signal channel from each detector to the coincidence counting circuit. This time lag is varied with each signal channel. It is therefore necessary to carry out timing correction for adjusting a delay time of each signal channel, so that the gamma rays will have the same timing of arrival at the coincidence counting circuit.

So, in carrying out such timing correction, calibration data is acquired using a radiation source (external radiation source) for calibration or simulated signals, and based on the calibration data, temporal variations in signal transmission are adjusted (see Patent Documents 1-3, for example). In recent years, a technique using time lag information (flight time) (TOF: Time Of Flight) has been proposed for localizing positron pair annihilation events (see Patent Document 4, for example). TOF is a technique for determining pair annihilation events, using that annihilation radiation is at light speed, by converting a time lag in arriving at detectors from the points of pair annihilation event into a distance difference from the points of pair annihilation event to light source generating positions by scintillator elements of the detectors.

The signal timing correction method described in Patent Document 1 noted above is as follows. The detectors detect radiation emitted from a radiation source, and timing signals indicating radiation incidence timing of radiation incident on the detectors are inputted to a coincidence counting circuit through delay adjusting circuits. In response to the input of these timing signals, outputs of the coincidence counting circuit are measured, to measure a sensitivity (that is, a count) of the radiation for each signal channel. Subsequently, the above sensitivity is measured while varying delay amounts adjusted by the delay adjusting circuits, to obtain a sensitivity distribution relative to the delay amount variations. The signal time lag is corrected by using in the delay adjusting circuit having a delay amount resulting in the highest measured sensitivity.

The signal timing correction method described in Patent Document 2 noted above is as follows. A radiation source (external radiation source) for calibration is installed in the field of view (FOV) of a PET apparatus. Here, a plurality of detectors are arranged in a ring (annularly). Regarding a certain detector as reference, timing values of a plurality of detectors sharing a field of view of the reference detector are averaged, and the averaged timing value is determined as a time delay value relative to the reference detector. A detector adjoining the reference detector is regarded as a new reference, and a time delay value is determined similarly. A difference between the time delay value determined first and the time delay value determined next is determined to serve as a reference correction value. Timing correction is carried out by uniforming times using the reference correction value. Subsequently, similar computations are carried out for successively adjoining detectors, to complete the timing correction when one circuit has been made of the ring.

The signal timing correction method described in Patent Document 3 noted above is as follows. Simulated signals outputted from a simulated signal generating device are inputted to a plurality of signal processing devices (signal processing units), respectively. Based on output of each signal processing device, calibration data is generated to carry out timing correction.

In Patent Document 4 noted above, a TOF type PET apparatus has incorporated therein DOI detectors which can discriminate light source positions having caused an interaction in a depth direction (DOI: Depth of Interaction). The DOI detectors are constructed of respective scintillator elements stacked in the depth direction of radiation (gamma rays here). Coordinates information in the depth direction in which the interaction has occurred and a transverse direction (direction parallel to the plane of incidence) is derived from centroid computations. Detection time correction information corresponding to this coordinates information is written to and stored in a table. By referring to the detection time correction information, information accuracy of flight time differences is improved.

[Patent Document 1]
Patent Publication H6-19436
[Patent Document 2]
Specification of U.S. Pat. No. 3,343,122
[Patent Document 3]
Unexamined Patent Publication No. 2006-90827
[Patent Document 4]
Unexamined Patent Publication No. 2008-51701

DISCLOSURE OF THE INVENTION

Problem to be Solved by the Invention

However, in the case of Patent Document 1 noted above, measurement must be repeated in order to determine the delay amount. In the case of Patent Document 2 noted above, time is not uniform among the plurality of detectors sharing the field of view of the reference detector. Therefore, time will not be uniformed completely even if the timing values of these detectors are averaged and one circuit is made of the ring using the averaged timing value as time delay value. As a result, it is necessary to repeat the above-noted computation after making a plurality of circuits (e.g. two to three circuits) of the ring until an optimal time delay value is obtained.

In the case of Patent Document 3 noted above, the simulated signal generating device is needed in addition to the detectors. Since only delays in the signal processing devices are corrected, detection time correction information cannot be obtained when, as in Patent Document 4 noted above, the detection time correction information corresponding to the coordinates information in the depth direction in which the annihilation radiation and the scintillator elements have caused an interaction and the transverse direction is required for the DOI detectors which discriminate light source positions in the depth direction in which the interaction has occurred.

This invention is made having regard to the state of the art noted above, and its object is to provide a positron CT apparatus and a timing correction method which enable coincidences to be counted accurately without repeating many measurements and computations.

MEANS FOR SOLVING THE PROBLEM

To fulfill the above object, this invention provides the following construction.

A positron CT apparatus of this invention is a positron CT apparatus having a plurality of detectors for detecting radiation released from a positron-emitting radioactive drug given to a patient, which comprises a computing device, in connection with a time lag histogram showing a count value distribution of time lag variations for each pair of detectors which count coincidences of the radiation, for selecting two target detectors which count coincidences, selecting one detector out of the two selected detectors, selecting a detector different from the other detector, and when repeating the selection, making a time lag histogram concerning two detectors selected in the past a reference, correcting a time lag histogram concerning detectors selected this time based on the reference, and repeating an operation to make the corrected time lag histogram concerning the two detectors a new reference; and a coincidence counting circuit for counting coincidences of the radiation based on the time lag histogram for each pair of detectors repeatedly corrected by the computing device.

According to the positron CT apparatus of this invention, the computing device carries out the following computations in connection with a time lag histogram showing a count value distribution of time lag variations for each pair of detectors which count coincidences of radiation. That is, two target detectors which count coincidences are selected.

One detector is selected out of the two selected detectors, and a detector different from the other detector is selected. When repeating the selection, a time lag histogram concerning two detectors selected in the past is made a reference, and based on this reference, a time lag histogram concerning two detectors selected this time is corrected. And an operation to make the corrected time lag histogram concerning the two detectors a new reference is repeated. Thus, the operation is repeated to make the time lag histogram concerning two detectors selected in the past a reference, and based on this reference, to correct the time lag histogram concerning two detectors selected this time, and make the time lag histogram concerning the two corrected detectors a new reference. This provides better convergence in obtaining an optimal time lag histogram than, for example, the case of averaging timing values of a plurality of detectors as in Patent Document 2 described hereinbefore. Therefore, an optimal time lag histogram can be obtained without repeating many measurements and computations. Since the coincidence counting circuit counts coincidences of radiation based on the time lag histogram of each pair of detectors corrected repeatedly as described above, the coincidences can be counted accurately. As a result, coincidence counting can be carried out accurately without repeating many measurements and computations.

A timing correction method of this invention is a timing correction method for use in counting coincidences of radiation released from a positron-emitting radioactive drug given to a patient, which comprises a histogram correcting step, in connection with a time lag histogram showing a count value distribution of time lag variations for each pair of detectors which count coincidences of the radiation, for selecting two target detectors which count coincidences, selecting one detector out of the two selected detectors, selecting a detector different from the other detector, and when repeating the selection, making a time lag histogram concerning two detectors selected in the past a reference, correcting a time lag histogram concerning detectors selected this time based on the reference, and repeating an operation to make the corrected time lag histogram concerning the two detectors a new reference.

According to the timing correction method of this invention, the histogram correcting step carries out the following correction in connection with a time lag histogram for each pair of detectors. That is, two target detectors which count coincidences are selected. One detector is selected out of the two selected detectors, and a detector different from the other detector is selected. When repeating the selection, a time lag histogram concerning two detectors selected in the past is made a reference, and based on this reference, a time lag histogram concerning two detectors selected this time is corrected. And an operation to make the corrected time lag histogram concerning the two detectors a new reference is repeated. As a result, timing correction can be carried out accurately without repeating many measurements and computations.

In one example of these positron CT apparatus and timing correction method described above, a time lag at which a total count value in the above time lag histogram made the reference becomes the largest is used as reference value, and time lags of the time lag histograms are corrected based on the above reference value. The temporal location where the total count value in the time lag histogram is the largest is a time at which coincidence counting is most likely to occur. Therefore, the times can be uniformed by correcting the time lags of the time lag histograms based on the reference value reflecting that time.

In another example of these positron CT apparatus and timing correction method described above, a time lag with a middle value between a time lag at which a total count value is the largest and a time lag at which the total count value is the second largest in the above time lag histogram made the reference is used as reference value, and time lags of the time lag histograms are corrected based on the above reference value. As described hereinafter, when the detectors have scintillator elements with self-radioactivity, the timing of radiation from the self-radioactivity of the scintillator element of one detector being detected in the largest amount by the scintillator element of the other detector, and the timing of radiation from the self-radioactivity of the scintillator element of the other detector being detected in the largest amount by the scintillator element of the one detector, are the temporal location where the total count value is the largest, or the temporal location where the total count value is the second largest. This means that the middle value between two time lags corresponding to these timings is a time at which coincidence counting is most likely to occur. Therefore, the times can be uniformed by correcting the time lags of the time lag histograms based on the reference value reflecting that time.

The above detectors, apart from a construction having a single scintillator element, may also be constructed to have a plurality of scintillator elements. With the latter construction, correction may be carried out for each scintillator element group (that is, in units of the detector) consisting of the plurality of scintillator elements. However, as described below, correction may be carried out for each unit of scintillator element consisting of one scintillator element, thereby to improve accuracy.

For example, the following computations and correction are carried out in connection with the time lag histogram for each pair of scintillator element units each consisting of one scintillator element of each of the detectors which count coincidences of the radiation. That is, two scintillator element units of target detectors which count coincidences are selected. One scintillator element unit of the detector is selected out of the two selected scintillator element units, and a scintillator element unit different from the other scintillator element unit of the detector is selected. When repeating the selection, a time lag histogram concerning two scintillator element units of detectors selected in the past is made a reference, and a time lag histogram concerning scintillator element units of detectors selected this time is corrected based on the reference. And an operation to make the corrected time lag histogram concerning the two scintillator element units of the detectors a new reference is repeated. Since correction is carried out for each scintillator element unit in this way, accuracy can be improved further, compared with carrying out correction for each detector unit.

For example, the following computations and correction are carried out in connection with the time lag histogram for each pair made of a scintillator element group consisting of a plurality of scintillator elements of one detector out of detectors which count coincidences of the radiation and a scintillator element unit consisting of one scintillator element of the other detector. That is, the scintillator element group of one detector and the scintillator element unit of the other detector out of target detectors which count coincidences are selected. The scintillator element group is selected out of the scintillator element group and the scintillator element unit selected, and a scintillator element unit different from the scintillator element unit of the other detector is selected. When repeating the selection, a time lag histogram concerning a scintillator element group and a scintillator element unit selected in the past is made a reference, and a time lag histogram concerning a scintillator element group and a scintillator element unit selected this time is corrected based on the reference. And an operation to make the corrected time lag histogram concerning the scintillator element group and the scintillator element unit a new reference is repeated. Since correction is carried out for each scintillator element group and scintillator element unit in this way, accuracy can be improved further, compared with carrying out correction for each detector unit. Computation time and the burden can be reduced, compared with carrying out correction for each scintillator element unit.

In the positron CT apparatus, the detectors may be DOI detectors constructed by stacking the respective scintillator elements in a depth direction of the radiation. By applying this invention to the DOI detectors, detection time correction information can be obtained when detection time correction information corresponding to coordinates information in the depth direction in which interactions have occurred is required as in Patent Document 4 described hereinbefore, for example.

The positron CT apparatus and timing correction method described above may provide an external radiation source which emits radiation corresponding in type to the radioactive drug noted hereinbefore, or a phantom which emits, from inside, radiation corresponding in type to the radioactive drug, the time lag histograms being acquired based on the radiation from the external radiation source or the phantom. The detectors may have scintillator elements with self-radioactivity, the time lag histograms being acquired based on radiation from the self-radioactivity.

EFFECTS OF THE INVENTION

According to the positron CT apparatus and timing correction method of this invention, two target detectors which count coincidences are selected. One detector is selected out of the two selected detectors, and a detector different from the other detector is selected. When repeating the selection, a time lag histogram concerning two detectors selected in the past is made a reference, and based on this reference, a time lag histogram concerning two detectors selected this time is corrected. And an operation to make the corrected time lag histogram concerning the two detectors a new reference is repeated. As a result, timing correction can be carried out accurately without repeating many measurements and computations.

DESCRIPTION OF REFERENCES

10 . . . coincidence counting circuit
11 . . . data collection and control unit
3 . . . gamma-ray detectors
31 . . . scintillator blocks
33 . . . photomultiplier tube (PMT)
RI . . . external radiation source
Ph . . . phantom
S . . . reference detector, reference scintillator element unit, reference scintillator element group
C . . . correction target detector, correction target scintillator element unit
O . . . opposite detector
M . . . patient

[Embodiment 1]

Figure 1:
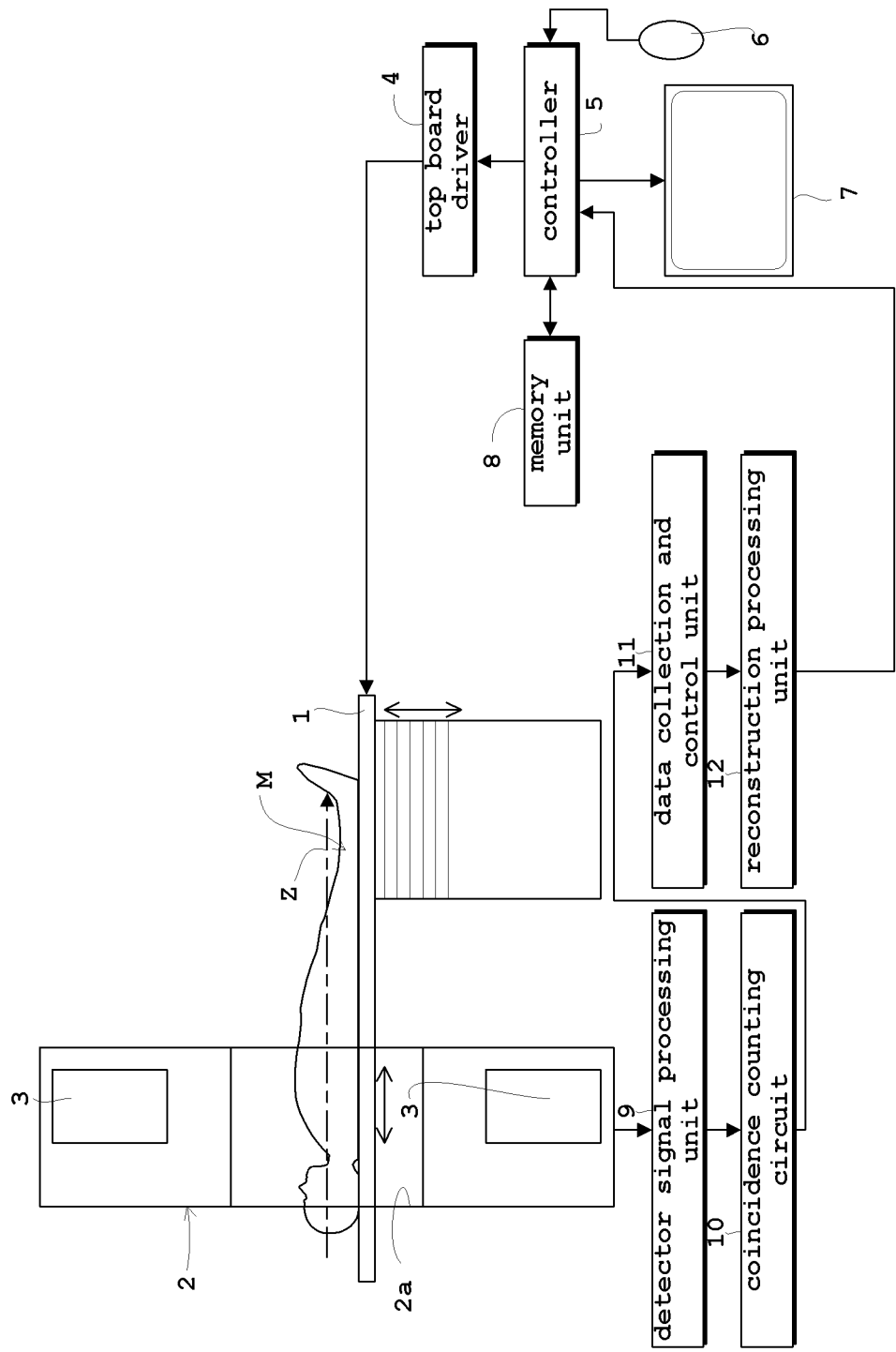
FIG. 1 is a side view and block diagram of a PET (Positron Emission Tomography) apparatus according to each embodiment.
Figure 2:
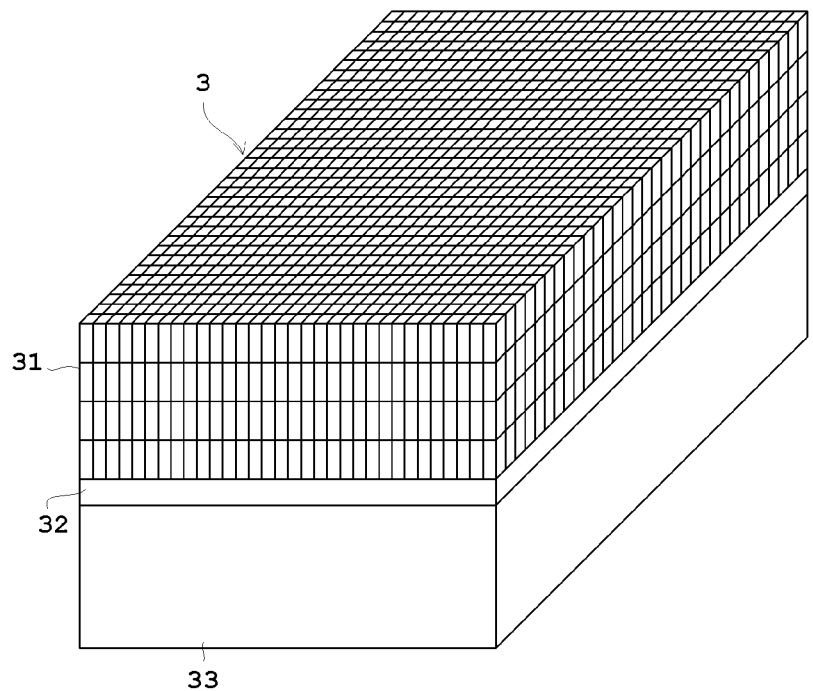
FIG. 2 is an outline perspective view of a gamma-ray detector.
Figure 3:
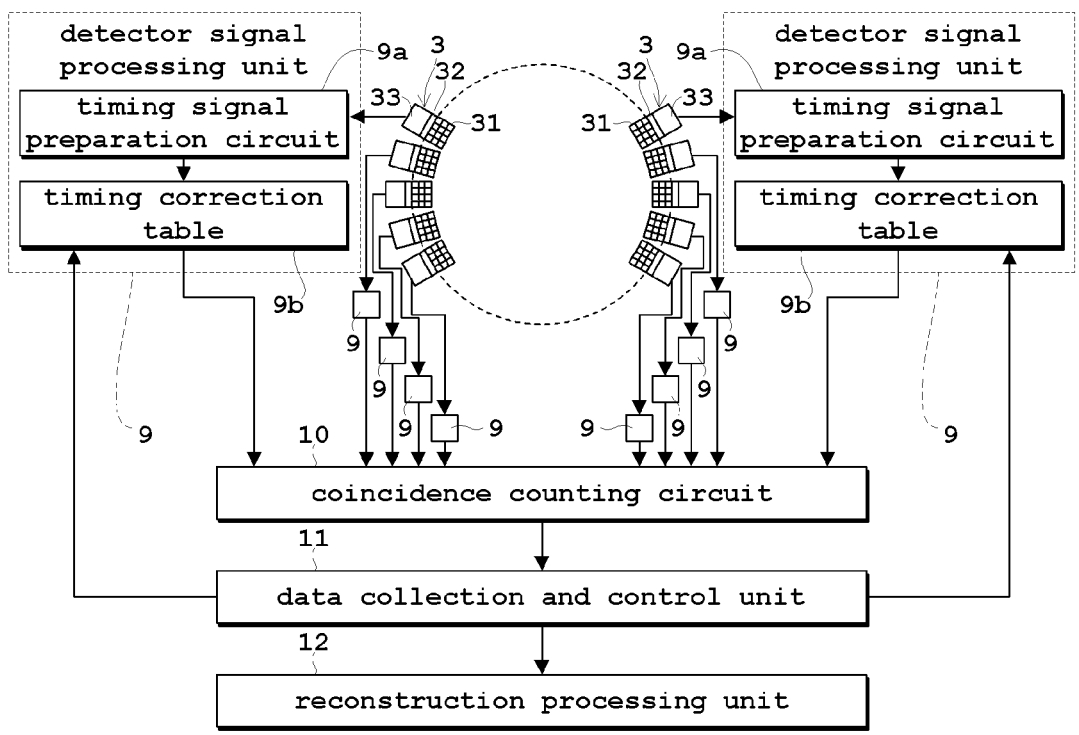
FIG. 3 is a front view of gamma-ray detectors arranged in a ring form in the PET apparatus and a block diagram relating thereto.

Embodiment 1 of this invention will be described hereinafter with reference to the drawings. FIG. 1 is a side view and block diagram of a PET (Positron Emission Tomography) apparatus according to Embodiment 1. FIG. 2 is an outline perspective view of a gamma-ray detector. FIG. 3 is a front view of gamma-ray detectors arranged in a ring form in the PET apparatus and a block diagram relating thereto.

The PET apparatus according to this Embodiment 1, including also Embodiments 2-4 described hereinafter, as shown in FIG. 1, includes a top board 1 for supporting a patient M. This top board 1 is constructed vertically movable up and down, and movable parallel to the body axis Z of the patient M. With such construction, the patient M placed on the top board 1 is passed through an opening 2a of a gantry 2 to be described hereinafter, and is scanned sequentially from the head to the abdomen and the feet, thereby obtaining images of the patient M. There is no specific limitation as to the sites to be scanned or the order in which the sites are scanned.

Besides the top board 1, the PET apparatus according to this Embodiment 1 includes the gantry 2 with the opening 2a, and gamma-ray detectors 3. The gamma-ray detectors 3 are arranged in a ring form so as to surround the body axis Z of the patient M, and are embedded in the gantry 2. The gamma-ray detectors 3 correspond to the detectors in this invention.

In addition, the PET apparatus according to this Embodiment 1 includes a top board driver 4, a controller 5, an input unit 6, an output unit 7, a memory unit 8, a detector signal processing unit 9, a coincidence counting circuit 10, a data collection and control unit 11, and a reconstruction processing unit 12. The top board driver 4 is a mechanism for driving the top board 1 to make the movements described above, and has a motor and the like not shown. The coincidence counting circuit 10 corresponds to the coincidence counting circuit in this invention, and the data collection and control unit 11 corresponds to the computing device in this invention.

The controller 5 performs overall control of the components forming the PET apparatus according to this Embodiment 1. The controller 5 and data collection and control unit 11 are formed of a central processing unit (CPU) and the like.

The input unit 6 feeds data and commands inputted by the operator into the controller 5. The input unit 6 is formed of pointing devices represented by a mouse, keyboard, joystick, trackball, touch panel and so on. The output unit 7 is formed of a display unit represented by a monitor, a printer and the like.

The memory unit 8 is formed of storage media represented by a ROM (Read-only Memory), RAM (Random-Access Memory) and so on. In this Embodiment 1, data relating to coincidence counting such as values of coincidence counting (counts) given by the coincidence counting circuit 10, detector pairs each consisting of two gamma-ray detectors 3 having counted coincidences, and LORs, and images resulting from processing by the reconstruction processing unit 12, are written to and stored in the RAM and are read from the RAM as necessary. The ROM stores beforehand programs for imaging, including various types of nuclear medicine diagnosis, for example. The programs are executed by the controller 5 and data collection and control unit 11 to carry out nuclear medicine diagnoses corresponding to the programs, respectively. The term LOR (Line Of Response) refers to a virtual straight line linking two gamma detectors 3 which count a coincidence.

The reconstruction processing unit 12 is realized, for example, by the controller 5 executing the programs stored in the ROM of the storage medium represented by the above memory unit 8, or the commands inputted by pointing devices represented by the input unit 6.

Scintillator blocks 31 (see FIG. 2) of each gamma-ray detector 3 convert into light gamma rays generating from the patient M medicated with a radioactive drug. A photomultiplier tube (PMT) 33 (see FIG. 2) of the gamma-ray detector 3 multiplies the converted light and converts it into an electric signal. The electric signal is inputted through the detector signal processing unit 9 to the coincidence counting circuit 10.

Specifically, when the patient M is medicated with the radioactive drug, two gamma rays will be generated by annihilation of a positron of a positron-emitting RI. The coincidence counting circuit 10 checks positions of the scintillator blocks 31 (see FIG. 2) and incidence timing of the gamma rays, and determines the inputted event to be proper data only when the gamma rays impinge on two scintillator blocks 31 at opposite sides of the patient M at the same time. When a gamma ray impinges on only one scintillator block 31, the coincidence counting circuit 10 discards it. That is, the coincidence counting circuit 10 detects, based on the above electric signals, that gamma rays are observed simultaneously by two gamma-ray detectors 3.

Among the electric signals inputted to the coincidence counting circuit 10, the electric signals simultaneously observed (that is, counted as coincidences) are determined to be image information. The image information is inputted through the data collection and control unit 11 to the reconstruction processing unit 12. The reconstruction processing unit 12 carries out image reconstruction by forward projection process and back projection process, and obtains images of the patient M. The images are sent to the output unit 7 through the controller 5. Thus, a nuclear medicine diagnosis is carried out based on the images obtained by the reconstruction processing unit 12. A known iterative approximation algorithm such as DRAMA (Dynamic Row-Action Maximum Likelihood Algorithm) is applied to the image reconstruction by the reconstruction processing unit 12. Specific functions of the detector signal processing unit 9 and data collection and control unit 11 will be described hereinafter.

The gamma-ray detector 3, as shown in FIG. 2, has scintillator blocks 31, a light guide 32 optically coupled to the scintillator blocks 31, and a photomultiplier tube (hereinafter abbreviated as "PMT") 33 optically coupled to the light guide 32. Each scintillator element forming the scintillator blocks 31 converts a gamma ray into light by emitting light in response to incidence of the gamma ray. The scintillator element detects the gamma ray through this conversion. The light emitted from the scintillator element is fully diffused in the scintillator blocks 31, and inputted to the PMT 33 through the light guide 32. The PMT 33 multiplies the light converted by the scintillator blocks 31, and converts it into an electric signal. The electric signal is sent through the detector signal processing unit 9 to the coincidence counting circuit 10 as described above. The scintillator blocks 31 correspond to the scintillator elements in this invention. The PMT 33 corresponds to the photoelectric conversion device in this invention.

To summarize the above, the gamma-ray detector 3 shown in FIG. 2 includes a plurality of scintillator blocks 31 which produce fluorescence upon incidence of gamma rays, and a PMT 33 which detects the gamma ray by carrying out photoelectric conversion of the light from each scintillator block 31. The gamma-ray detector 3 shown in FIG. 2 is a DOI detector with the respective scintillator blocks 31 stacked (stacked in four layers in FIG. 2) in the depth direction of the gamma rays.

When the coincidence counting circuit 10 counts coincidences, a signal time lag occur in a signal channel from each gamma-ray detector 3 to the coincidence counting circuit 10, thereby making accurate coincidence counting impossible. So, before a nuclear medicine diagnosis using the patient M, data for correction obtained beforehand using an external radiation source or a phantom is sent to the data collection and control 11 through the detector signal processing units 9 and coincidence counting circuit 10 as shown in FIG. 3, to allow the data collection and control unit 11 to collect the data. Then, the data collection and control unit 11 carries out timing correction through feedback control of the collected data for correction to timing correction tables 9b of the detector signal processing units 9.

In a usual image pickup for nuclear medicine diagnosis using a patient M, the gamma-ray detectors 3 detect gamma rays generating from the patient M medicated with a radioactive drug, and send them via the detector signal processing units 9 and coincidence counting circuit 10 and through the data collection and control unit 11 to the reconstruction processing unit 12 without timing correction. In data collection using the external radiation source or phantom, on the other hand, the gamma-ray detectors 3 detect gamma rays from the external radiation source or phantom, and send them via the detector signal processing units 9 and coincidence counting circuit 10 to the data collection and control unit 11. The data collection and control unit 11 carries out feedback control to the timing correction tables 9b of the detector signal processing units 9 for timing correction, and adjusts each delay amount in the coincidence counting circuit 10.

The detector signal processing units 9 include timing signal preparation circuits 9a for preparing signals indicating gamma-ray incidence times (hereinafter also called "time stamps") based on the electric signals outputted from the PMTs 33 of the gamma-ray detectors 3, and the above-mentioned timing correction tables 9b. As described above, the gamma-ray detectors 3 are arranged in a ring form, and each gamma-ray detector 3 is connected to the timing signal preparation circuit 9a of the detector signal processing unit 9 (only two timing signal preparation circuits 9a being shown in FIG. 3). The timing signal preparation circuits 9a are connected to the timing correction tables 9b, and the timing correction tables 9b are connected to the coincidence counting circuit 10. By connecting to the timing correction tables 9b the data collection and control unit 11 connected to the coincidence counting circuit 10, the data collection and control unit 11 carries out feedback control to the timing correction tables 9b.

Figure 4:
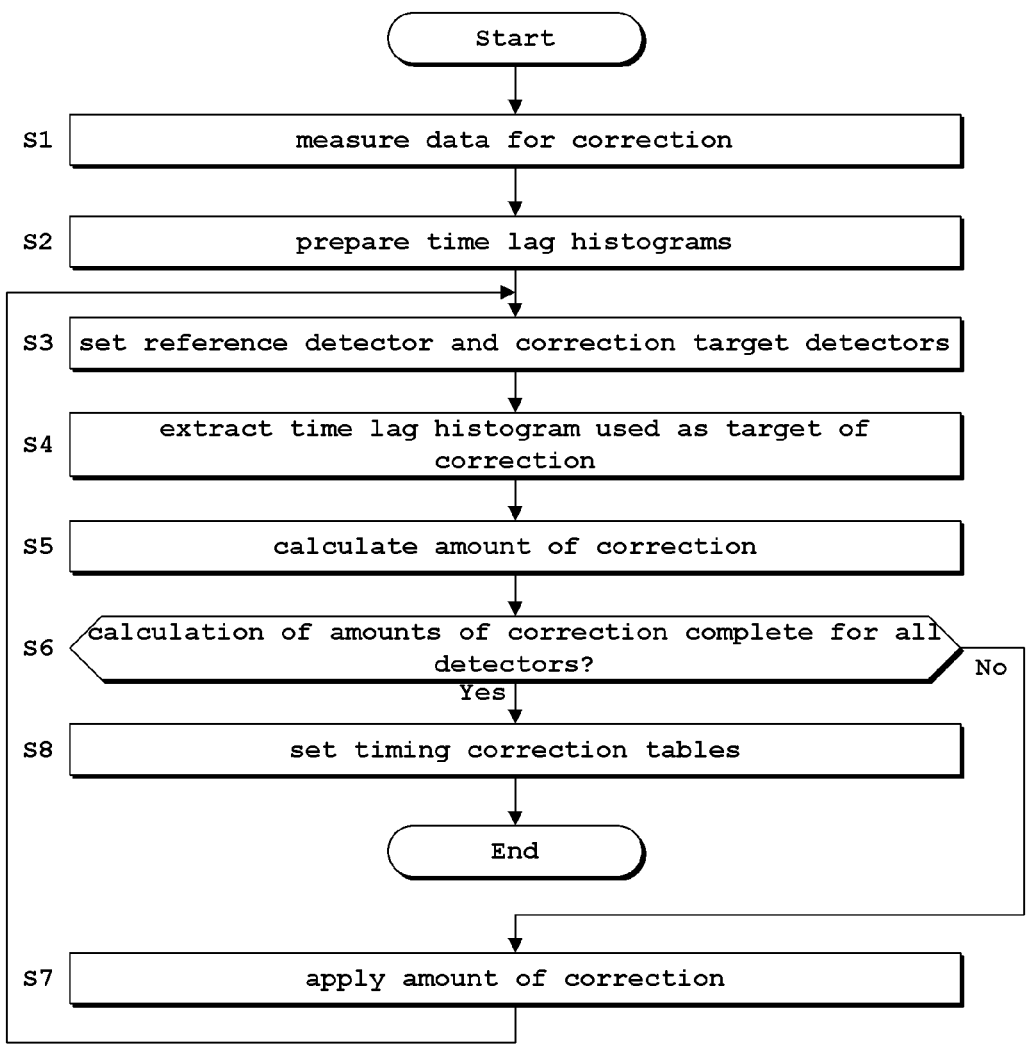
FIG. 4 is a flow chart showing a sequence of a timing correction method.
Figure 5:
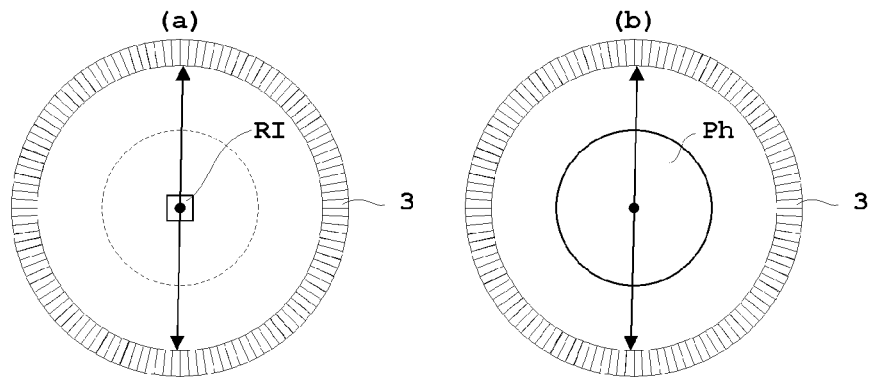
FIG. 5 (*a*) is a front view of the gamma-ray detectors when an external radiation source is placed, and (*b*) is a front view of the gamma-ray detectors when a phantom is placed.
Figure 6:
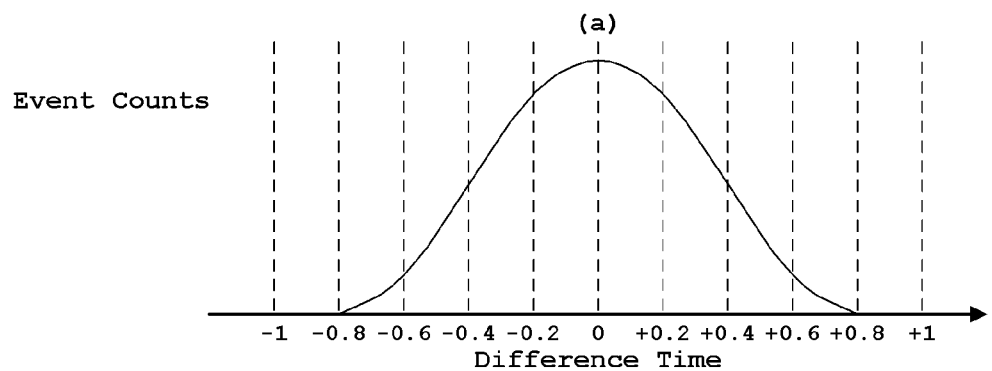
FIGS. 6 (*a*) and (*b*) are explanatory views of time lag histograms.
Figure 6:
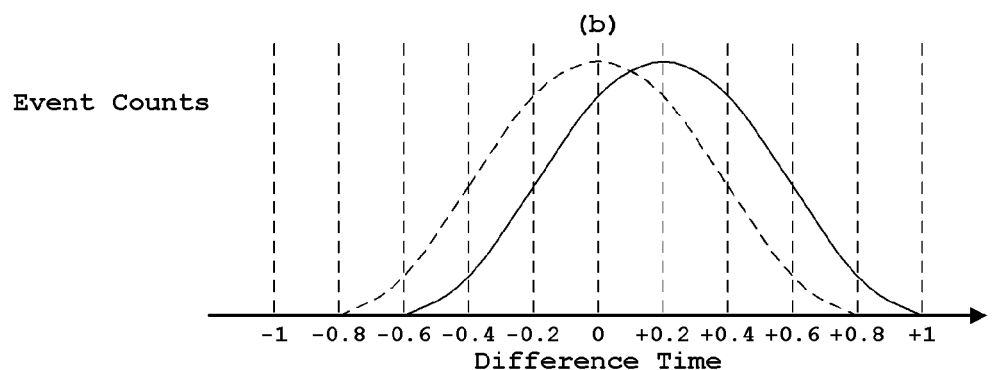
Figure 7:
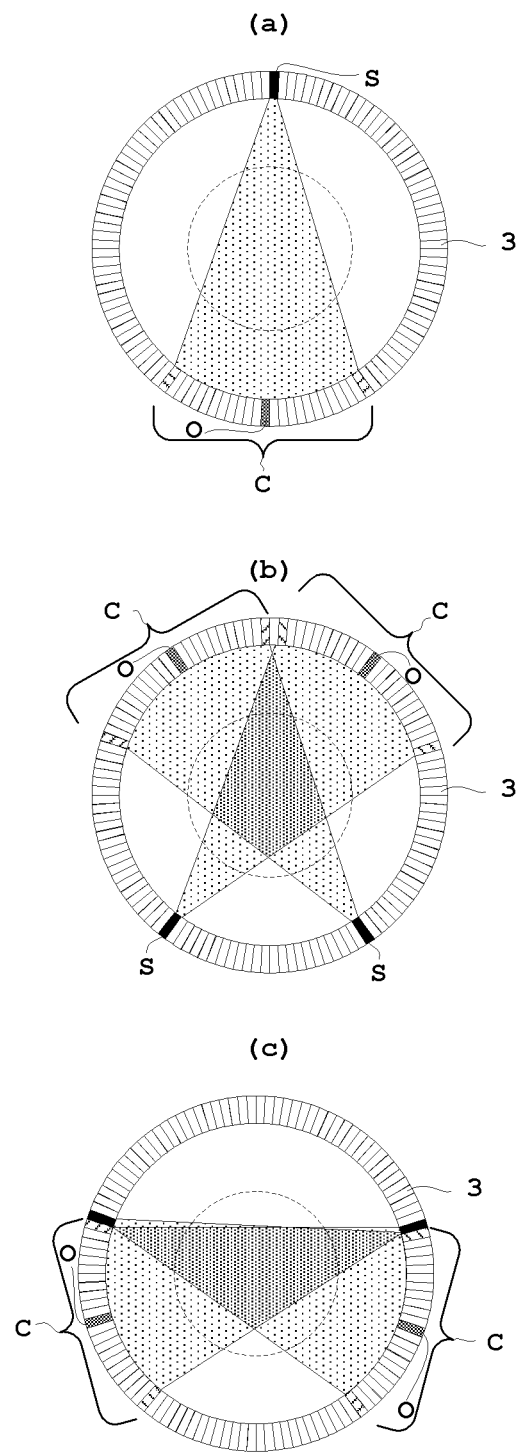
FIGS. 7 (*a*)-(*c*) are front views showing one embodiment of switching between reference detector and correction target detector.
Figure 8:
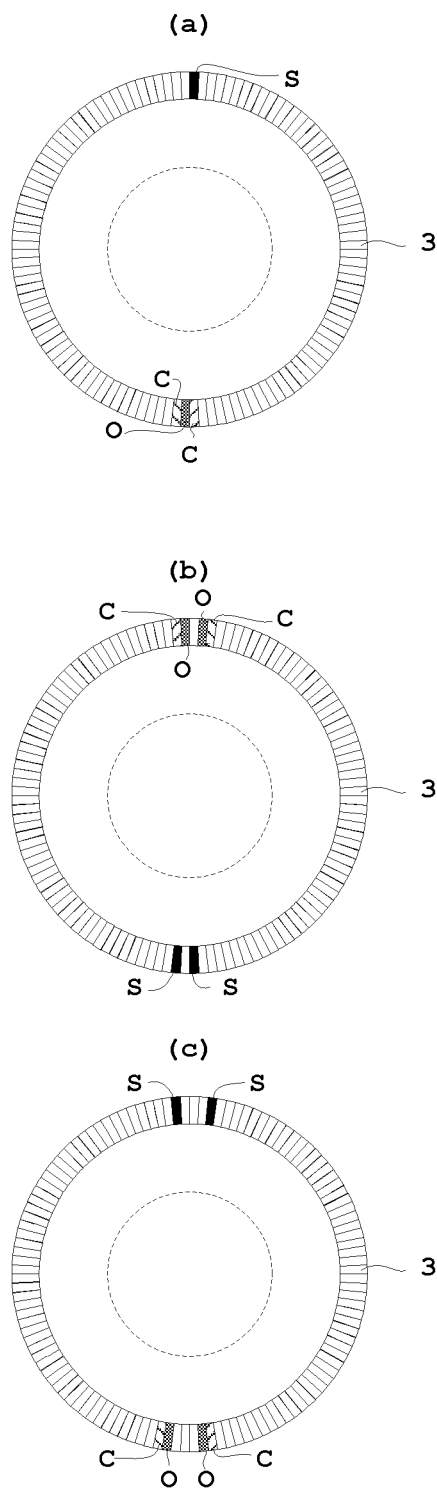
FIGS. 8 (*a*)-(*c*) are front views showing one embodiment, different from the embodiment of FIG. 7, of switching between reference detector and correction target detector.

Next, the timing correction will be described with reference to FIGS. 4-8. FIG. 4 is a flow chart showing a sequence of a timing correction method. FIG. 5 is a front view of the gamma-ray detectors when an external radiation source or a phantom is placed. FIG. 6 is an explanatory view of time lag histograms. FIG. 7 is a front view showing one embodiment of switching between reference detector and correction target detector. FIG. 8 is a front view showing one embodiment, different from the embodiment of FIG. 7, of switching between reference detector and correction target detector.

(Step S1) Measure Data for Correction

As shown in FIG. 5 (a), an external radiation source RI which emits radiation (gamma rays in this Embodiment 1) corresponding in type to a radioactive drug, i.e. radioisotope (RI), is placed in the field of view of the PET apparatus. Preferably, the external radiation source RI is placed in a central area within the field of view, whereby two gamma-ray detectors 3 about 180° opposite each other can detect the radiation from the external radiation source RI substantially simultaneously, and only a signal time lag in the signal channel from each gamma-ray detector 3 to the coincidence counting circuit 10 becomes a target of the timing correction. Therefore, times at which the gamma rays arrive at the coincidence counting circuit 10 can be brought into agreement only by carrying out the timing correction. Apart from the external radiation source RI, as shown in FIG. 5 (b), a phantom Ph which emits, from inside, radiation corresponding in type to the radioactive drug may be placed in the field of view of the PET apparatus. When placing the phantom Ph also, it preferably is placed in the central area within the field of view. The external radiation source RI corresponds to the external radiation source in this invention. The phantom Ph corresponds to the phantom in this invention.

The gamma-ray detectors 3 detect the radiation from the external radiation source RI or phantom Ph to acquire it as data for correction, and send it to the coincidence counting circuit 10 through the detector signal processing units 9. The data for correction is measured and acquired for all the gamma-ray detectors 3 as shown in FIG. 5.

(Step S2) Prepare Time Lag Histograms

Based on the data for correction measured in step S1, a time lag histogram is prepared for each pair of gamma-ray detectors 3 which count coincidences of the radiation. As shown in FIG. 6, the time lag histogram is a count value distribution of time lag variations, in which the horizontal axis represents a difference in time stamp (i.e. time lag) between each pair of gamma-ray detectors 3 (indicated "Difference Time" in FIG. 6), and the vertical axis represents count values (indicated "Event Counts" in FIG. 6).

When the external radiation source RI or phantom Ph is placed in the central area of the field of view, the time lag histogram is obtained as a frequency distribution centering on "0" as shown in FIG. 6 (a). However, when there is a shift due to a time lag, the time lag histogram shifts sideways as shown in a solid line in FIG. 6 (b). So, a shift amount for returning the time lag histogram from the solid line in FIG. 6 (b) to the frequency distribution centering on "0" shown in a dotted line is considered an amount of correction.

(Step S3) Set Reference Detector and Correction Target Detector

Next, a reference detector and correction target detectors are set, respectively. As shown in FIG. 7 (a), one gamma-ray detector 3 is set as reference, and this gamma-ray detector 3 set as reference (see the blackening in FIG. 7 (a)) is regarded as reference detector S. Pairing gamma-ray detectors 3 falling in the field of view of the PET apparatus seen from this reference detector S are set as targets of the correction. These gamma-ray detectors 3 set as targets of the correction are regarded as correction target detectors C.

From among these correction target detectors C, a gamma-ray detector 3 about 180° opposite the reference detector S is selected. With consecutive numbers given clockwise from the reference detector S regarded as gamma-ray detector 3 No. "1", in the case of 120 gamma-ray detectors 3 in all as shown in FIG. 7, gamma-ray detector 3 No. "61" is a gamma-ray detector 3 which is 180° opposite the reference detector S. In the case of an odd number of gamma-ray detectors in all, a 180° opposite gamma-ray detector 3 cannot be selected, and in such a case a gamma-ray detector 3 about 180° opposite may be selected. The gamma-ray detector 3 about 180° opposite the reference detector S (see the gray in FIG. 7 (a)) is regarded as opposite detector O.

Thus, in selecting two gamma-ray detectors 3 which count coincidences, the embodiment shown in FIG. 7 selects the reference detector S which is gamma-ray detector 3 No. "1" and the gamma-ray detector 3 No. "61" (opposite detector O) 180° opposite thereto. The time lag histogram concerning the selected reference detector S which is gamma-ray detector 3 No. "1" and gamma-ray detector 3 No. "61" (opposite detector O) which is 180° opposite thereto is used as reference. This time lag histogram made the reference is the frequency distribution centering on "0" as shown in FIG. 6 (a). Therefore, a time lag at which a total count value in the time lag histogram made the reference becomes the largest is set to "0", and this time lag "0" serves as reference value.

(Step S4) Extract Time Lag Histogram Used as Target of Correction

Of the two gamma-ray detectors 3 which consist of the reference detector S and opposite detector O selected in step S3, the reference detector S is selected as one gamma-ray detector 3, and correction target detectors C different from the opposite detector O which is the other gamma-ray detector 3 are selected. That is, correction target detectors C other than the opposite detector O and the reference detector S are selected, respectively, to select time lag histograms as targets of the correction. In the case shown in FIG. 7 (a), in step S3, the correction target detectors C including also gamma-ray detector 3 No. "61" (opposite detector O) are a total of 25 gamma-ray detectors 3 No. "49"-No. "73". A time lag histogram concerning the reference detector S which is gamma-ray detector 3 No. "1" and each of the correction target detectors C No. "49"-No. "60" and No. "62"-No. "73" other than gamma-ray detector 3 No. "61" (opposite detector O), is extracted as a time lag histogram concerning the two gamma-ray detectors 3 selected this time.

(Step S5) Calculate Amount of Correction

The time lag histogram concerning a correction target detector C other than the opposite detector O and the reference detectors S has a shift relative to the time lag histogram made the reference and, as described hereinbefore, is shifted sideways as shown in the solid line in FIG. 6 (b). So, the data collection and control unit 11 determines, as an amount of correction, a shift amount for returning the time lag histogram concerning the two gamma-ray detectors 3 selected this time in step S4, from the solid line of FIG. 6 (b) to the frequency distribution centering on "0" shown in the dotted line.

(Step S6) Calculation of Amounts of Correction Complete for all Detectors?

Determination is made as to whether calculation of the amounts of correction is completed for all the gamma-ray detectors 3. When not completed, the process moves to step S7. When completed, the process moves to step S8.

(Step S7) Apply Amount of Correction

Each of the time lag histograms is corrected by applying the amount of correction calculated in step S5 to shift the time lag histogram concerning the two gamma-ray detectors 3 selected this time, by the amount of correction back to the frequency distribution centering on "0". That is, each of the time lag histograms is corrected based on the time lag "0" which is the reference value. In the case shown in FIG. 7 (a), the time lag histogram concerning the reference detector S which is gamma-ray detector 3 No. "1" and each of the correction target detectors C No. "49"-No. "60" and No. "62"-No. "73" is corrected based on the time lag histogram concerning the reference detector S which is gamma-ray detector 3 No. "1" and gamma-ray detector 3 No. "61" (opposite detector O) 180° opposite thereto selected in the past. When the correction has been made by applying the amount of correction in step S7, the process returns to step S3 to carry out operations to set, as new references, two gamma-ray detectors 3 corrected in step S7. In the case shown in FIG. 7 (a), for example, out of the correction target detectors C No. "49"-No. "60" and No. "62"-No. "73", gamma-ray detectors 3 No. "49" and No. "73" (see slashes in FIG. 7 (a)) at the opposite ends of the correction target detectors C are made the new references.

And, in step S3, as shown in FIG. 7 (b), gamma-ray detector 3 No. "49" and gamma-ray detector 3 No. "73" (see the blackening in FIG. 7 (b)) are regarded as reference detectors S. In the same way as in FIG. 7 (a), pairing gamma-ray detectors 3 falling in the field of view of the PET apparatus seen from each reference detector S are set as targets of the correction. The gamma-ray detectors 3 set as targets of the correction are regarded as correction target detectors C. Here, the correction target detectors C are a total of 24 gamma-ray detectors 3 No. "97"-No. "120" for the reference detector S which is gamma-ray detector 3 No. "49", and a total of 24 gamma-ray detectors 3 No. "2"-No. "25" for the reference detector S which is gamma-ray detector 3 No. "73".

The reference detector S which is gamma-ray detector 3 No. "49" and gamma-ray detector 3 No. "109" (opposite detector O) (see gray in FIG. 7 (b)) 180° opposite thereto are selected. And the reference detector S which is gamma-ray detector 3 No. "73" and gamma-ray detector 3 No. "13" (opposite detector O) (see gray of FIG. 7 (b)) 180° opposite thereto are selected.

In the same way as in FIG. 7 (a), in step S4, a time lag histogram concerning the reference detector S which is gamma-ray detector 3 No. "49" and each of the correction target detectors C No. "97"-No. "108" and No. "110"-No. "120" other than gamma-ray detector 3 No. "109" (opposite detector O), is extracted as a time lag histogram concerning the two gamma-ray detectors 3 selected this time. Also in step S4, a time lag histogram concerning the reference detector S which is gamma-ray detector 3 No. "73" and each of the correction target detectors C No. "2"-No. "12" and No. "14"-No. "25" other than gamma-ray detector 3 No. "13" (opposite detector O), is extracted as a time lag histogram concerning the two gamma-ray detectors 3 selected this time.

In the same way as in FIG. 7 (a), an amount of correction is calculated in step S5, and whether calculation of the amount of correction is completed is determined in step S6. When not completed, the process moves to step S7. And in step S7 correction is made by applying the amount of correction, and the process returns to step S3 to carry out operations to set, as new references, two gamma-ray detectors 3 corrected in step S7. In the case shown in FIG. 7 (b), for example, out of the correction target detectors C corrected, gamma-ray detectors 3 No. "25" and No. "97" at the lower ones of the four opposite ends of the correction target detectors C (see slashes in FIG. 7 (b)) are made the new references.

And, in step S3, as shown in FIG. 7 (c), gamma-ray detector 3 No. "25" and gamma-ray detector 3 No. "97" (see the blackening in FIG. 7 (b)) are regarded as reference detectors S. Pairing gamma-ray detectors 3 falling in the field of view of the PET apparatus seen from each reference detector S are set as targets of the correction. The gamma-ray detectors 3 set as targets of the correction are regarded as correction target detectors C. Here, the correction target detectors C are a total of 23 gamma-ray detectors 3 No. "74"-No. "96" for the reference detector S which is gamma-ray detector 3 No. "25", and a total of 23 gamma-ray detectors 3 No. "26"-No. "48" for the reference detector S which is gamma-ray detector 3 No. "97".

The reference detector S which is gamma-ray detector 3 No. "25" and gamma-ray detector 3 No. "85" (opposite detector O) (see gray in FIG. 7 (c)) 180° opposite thereto are selected. And the reference detector S which is gamma-ray detector 3 No. "97" and gamma-ray detector 3 No. "37" (opposite detector O) (see gray of FIG. 7 (c)) 180° opposite thereto are selected.

In step S4, a time lag histogram concerning the reference detector S which is gamma-ray detector 3 No. "25" and each of the correction target detectors C No. "74"-No. "84" and No. "86"-No. "96" other than gamma-ray detector 3 No. "85" (opposite detector O), is extracted as a time lag histogram concerning the two gamma-ray detectors 3 selected this time. Also in step S4, a time lag histogram concerning the reference detector S which is gamma-ray detector 3 No. "97" and each of the correction target detectors C No. "26"-No. "36" and No. "38"-No. "48" other than gamma-ray detector 3 No. "37" (opposite detector O), is extracted as a time lag histogram concerning the two gamma-ray detectors 3 selected this time.

An amount of correction is calculated in step S5, and whether calculation of the amount of correction is completed is determined in step S6. When not completed, the process moves to step S7. And in step S7 correction is made by applying the amount of correction, and the process returns to step S3. With this third repetitive loop of steps S6, S7 and S3-S5, amounts of correction for all the gamma-ray detectors 3 No. "1" to No. "120" have been completed, and the completion is determined in step S6. Then, the process moves to step S8. These steps S3-S6 described above correspond to the histogram correcting step in this invention.

(Step S8) Set Timing Correction Tables

Timing correction tables are set by writing the amounts of correction calculated in these steps S3-S6 (three repetitive loops in the embodiment of FIG. 7) from the data collection and control unit 11 to the timing correction tables 9b of the detector signal processing units 9. By applying these set amounts of correction to an ordinary image pickup in a nuclear medicine diagnosis using a patient M, it is possible to adjust timing with high precision, and images of excellent image quality can be acquired when carrying out the above image pickup.

In the embodiment of FIG. 7, it was the case of 120 gamma-ray detectors 3 in all, but the number of gamma-ray detectors is not limitative. An outline of setting of reference detectors S and correction target detectors O when there are 88 gamma-ray detectors 3 in all, is as follows. In the first loop, correction target detectors C for the reference detector S which is gamma-ray detector 3 No. "1", are a total of 19 gamma-ray detectors 3 No. "36"-No. "54" (opposite detector O being No. "45"). After correction, gamma-ray detectors 3 No. "36" and "54" at the opposite ends of the correction target detectors C are selected as new references.

In the second loop, correction target detectors C for the reference detector S which is gamma-ray detector 3 No. "36", are a total of 18 gamma-ray detectors 3 No. "71"-No. "88" (opposite detector O being No. "80"), and those for the reference detector S which is gamma-ray detector 3 No. "54", are No. "2"-No. "19" (opposite detector O being No. "10"). After correction, gamma-ray detectors 3 No. "19" and "71" at the lower ones of the four opposite ends of the correction target detectors C are selected as new references.

In the third loop, correction target detectors C for the reference detector S which is gamma-ray detector 3 No. "19", are a total of 16 gamma-ray detectors 3 No. "55"-No. "70" (opposite detector O being No. "63"), and those for the reference detector S which is gamma-ray detector 3 No. "71", are No. "20"-No. "35" (opposite detector O being No. "27").

Thus, also in the case of 88 gamma-ray detectors 3 in all, the third repetitive loop of steps S6, S7 and S3-S5 completes calculation of amounts of correction for all the gamma-ray detectors 3 No. "1" to No. "88".

In the embodiment of FIG. 7, the loop count of steps S6, S7 and S3-S5 was three times, but the loop count is not limitative. An outline of setting of reference detectors S and correction target detectors O in the embodiment of FIG. 8 is set out below, for example. In the first loop, as shown in FIG. 8 (a), a reference detector S which is gamma-ray detector 3 No. "1", and gamma-ray detector 3 No. "61" (opposite detector O) 180° opposite thereto, are selected, and gamma-ray detectors 3 No. "60" and No. "62" on both sides of the opposite detector O are made correction target detectors C.

The time lag histogram concerning the selected reference detector S which is gamma-ray detector 3 No. "1" and gamma-ray detector 3 No. "61" (opposite detector O) which is 180° opposite thereto is used as reference. Out of the two selected gamma-ray detectors 3 consisting of the reference detector S which is gamma-ray detector 3 No. "1" and gamma-ray detector 3 No. "61" (opposite detector O), the reference detector S is selected as one gamma-ray detector 3, and the above-noted correction target detectors C No. "60" and "62" different from the opposite detector O which is the other gamma-ray detector 3 are selected.

Based on the time lag histogram concerning the reference detector S, which is gamma-ray detector 3 No. "1", and gamma-ray detector 3 No. "61" (opposite detector O) 180° opposite thereto selected in the past, the time lag histogram concerning the reference detector S which is gamma-ray detector 3 No. "1" and correction target detector C No. "60" selected this time is corrected, and the time lag histogram concerning the reference detector S which is gamma-ray detector 3 No. "1" and correction target detector C No. "62" also selected this time is corrected. After the correction, the correction target detectors C, i.e. gamma-ray detector 3 No. "60" and gamma-ray detector 3 No. "62", are made new references.

In the second loop, as shown in FIG. 8 (b), the correction target detectors C are gamma-ray detector 3 No. "119" adjoining the opposite detector O No. "120" for the reference detector S which is gamma-ray detector 3 No. "60", and gamma-ray detector 3 No. "3" adjoining the opposite detector O No. "2" for the reference detector S which is gamma-ray detector 3 No. "62". Gamma-ray detector 3 No. "1" adjoining the opposite detector O No. "120" and adjoining the opposite detector O No. "2" has already been selected and is therefore excluded. After correction, correction target detectors C No. "3" and No. "119" are made new references.

In the third loop, as shown in FIG. 8 (c), the correction target detectors C are gamma-ray detector 3 No. "64" adjoining the opposite detector O No. "63" for the reference detector S which is gamma-ray detector 3 No. "3", and gamma-ray detector 3 No. "58" adjoining the opposite detector O No. "59" for the reference detector S which is gamma-ray detector 3 No. "119". Gamma-ray detector 3 No. "60" adjoining the opposite detector O No. "59" and gamma-ray detector 3 No. "62" adjoining the opposite detector O No. "63" have already been selected and are therefore excluded. After correction, correction target detectors C No. "58" and No. "64" are made new references.

Subsequently, the repetitive loop of steps S6, S7 and S3-S5 is carried out until calculation of the amounts of correction for all the gamma-ray detectors 3 No. "1" to No. "120" is completed.

The series of timing corrections shown in FIG. 4, preferably, is carried out periodically according to secular changes of the time lag of each channel. Further, it is preferable to make the correction tables into files and write and store them in the storage medium of the data collection and control unit 11 or in the memory unit 8 noted hereinbefore, and when the power of the PET apparatus is turned off and turned on again for startup, to read them from the storage medium or memory unit 8 and write them in the timing correction tables 9b again.

According to the PET apparatus and the timing correction method in this Embodiment 1 having the above construction, the data collection and control unit 11 carries out the following correcting operations in steps S3-S6 in connection with a time lag histogram showing a count value distribution of time lag variations for each pair of gamma-ray detectors 3 which count coincidences of radiation (gamma rays in this Embodiment 1). That is, two target gamma-ray detectors 3 which count coincidences are selected (reference detector S No. "1" and opposite detector O No. "61" 180° opposite thereto in the case of FIG. 7 (*a*)). The reference detector S is selected which is one detector out of the two selected gamma-ray detectors 3, and gamma-ray detectors 3 (correction target detectors C No. "49"-No. "60" and No. "62"-No. "73" in the case of FIG. 7 (*a*)) different from the other, opposite detector O are selected. When repeating the selection, the time lag histogram concerning the two gamma-ray detectors 3 selected in the past (reference detector S No. "1" and opposite detector O No. "61" 180° opposite thereto in the case of FIG. 7 (*a*)) is made a reference, and based on this reference, the time lag histogram concerning the two gamma-ray detectors 3 selected this time is corrected. And an operation to make the corrected time lag histogram concerning the two gamma-ray detectors 3 a new reference is repeated (see the repetitive loops of steps S6, S7, and S3-S5 in FIG. 4).

Thus, the operation is repeated to make the time lag histogram concerning two gamma-ray detectors 3 selected in the past a reference, and based on this reference, to correct the time lag histogram concerning two gamma-ray detectors 3 selected this time, and make the time lag histogram concerning the two corrected gamma-ray detectors 3 a new reference. This provides better convergence in obtaining an optimal time lag histogram than, for example, the case of averaging timing values of a plurality of detectors as in Patent Document 2 described hereinbefore. Therefore, an optimal time lag histogram can be obtained without repeating many measurements and computations.

Since the coincidence counting circuit 10 counts coincidences of radiation (gamma rays in this Embodiment 1) based on the time lag histogram of each pair of gamma-ray detectors 3 corrected repeatedly as described above, the coincidences can be counted accurately. As a result, coincidence counting and timing correction can be carried out accurately without repeating many measurements and computations.

In this Embodiment 1, a time lag at which a total count value in the time lag histogram made the above reference becomes the largest is used as reference value, and the time lags of the time lag histograms are corrected based on the above reference value. The temporal location where the total count value in the time lag histogram is the largest is a time at which coincidence counting is most likely to occur. Therefore, the times can be uniformed by correcting the time lags of the time lag histograms based on the reference value reflecting that time.

In this Embodiment 1, correction is carried out for each scintillator element group (that is, in units of the detector) consisting of a plurality of scintillator elements (scintillator blocks 31). The gamma-ray detectors 3 in this Embodiment 1 are DOI detectors constructed by stacking the scintillator blocks 31 in the depth direction of gamma rays. By applying this invention to the DOI detectors as in this Embodiment 1, detection time correction information can be obtained when detection time correction information corresponding to coordinates information in the depth direction in which interactions have occurred is required as in Patent Document 4 described hereinbefore, for example. That is, after carrying out the series of timing corrections shown in FIG. 4, light source positions in the depth direction are determined by centroid calculation, to obtain detection time correction information corresponding to coordinates information in the depth direction, for example.

This Embodiment 1 provides the external radiation source RI which emits radiation corresponding in type to a radioactive drug, or the phantom Ph which emits, from inside, radiation corresponding in type to the radioactive drug. The above time lag histograms are acquired based on the radiation from the external radiation source RI or phantom Ph.

[Embodiment 2]

Figure 9:
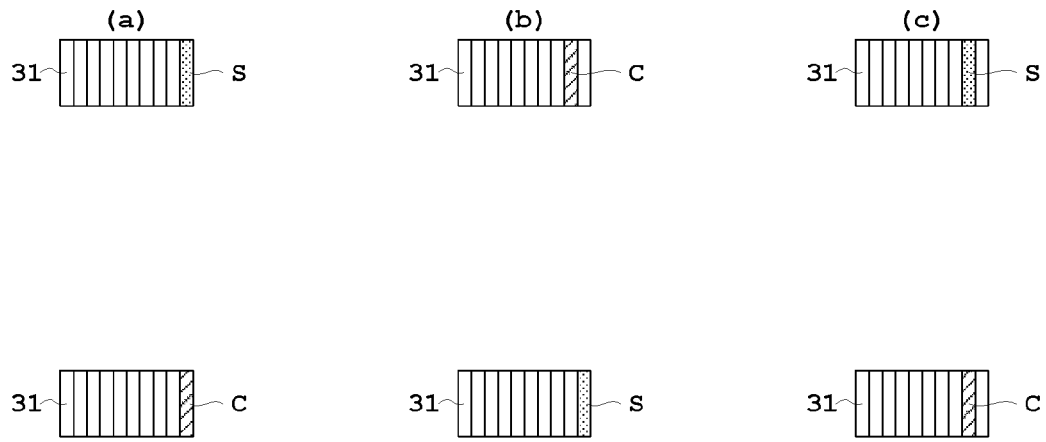
FIGS. 9 (*a*)-(*c*) are front views showing one embodiment of switching between reference scintillator element unit and correction target scintillator element unit.

Next, Embodiment 2 of this invention will be described with reference to the drawings. FIG. 9 is a front view showing one embodiment of switching between reference scintillator element unit and correction target scintillator element unit. The PET apparatus according to this Embodiment 2, including also Embodiments 3 and 4 described hereinafter, is the block diagram shown in FIG. 1. Components common to Embodiment 1 described hereinbefore will be affixed with the same reference signs, and their description will be omitted.

In Embodiment 1 described hereinbefore, correction is carried out for each scintillator element group (that is, in units of the detector) consisting of a plurality of scintillator elements (scintillator blocks 31). In this Embodiment 2, including also Embodiment 3 described hereinafter, correction is carried out for each unit of scintillator element consisting of one scintillator element as described below, thereby to improve accuracy. FIG. 9 shows only the scintillator blocks 31, and the other components (light guides 32 and PMTs 33) are excluded from the illustration.

A reference scintillator element unit and a correction target scintillator element unit of gamma-ray detectors which count coincidences are set, respectively. As shown in FIG. 9 (*a*), one scintillator block 31 of a certain gamma-ray detector is set as reference, and the one scintillator block 31 set as reference is regarded as a reference scintillator element unit S. One scintillator block 31 of a gamma-ray detector different from the reference scintillator element unit S is set as correction target, and the one scintillator block 31 set as correction target is regarded as a correction target scintillator element unit C. Since the specific timing correction is the same technique excepting that a change is made from the detector unit in Embodiment 1 to the scintillator element unit in Embodiment 2, its description is omitted.

As shown in FIG. 9 (*b*), the correction target scintillator element unit C after correction is set as new reference to be regarded as reference scintillator element unit S. One scintillator block 31 of a gamma-ray detector different from the reference scintillator element unit S is set as correction target, and the one scintillator block 31 set as correction target is regarded as a correction target scintillator element unit C.

And, as shown in FIG. 9 (*c*), the correction target scintillator element unit C, after correction, is set as new reference to be regarded as reference scintillator element unit S. One scintillator block 31 of a gamma-ray detector different from the reference scintillator element unit S is set as correction target, and the one scintillator block 31 set as correction target is regarded as a correction target scintillator element unit C. In this way, timing correction is carried out similarly for scintillator element units of the other detectors.

According to the PET apparatus and the timing correction method in this Embodiment 2 having the above construction, two scintillator element units of target gamma-ray detectors which count coincidences are selected, and out of the two selected scintillator element units, the scintillator element unit (reference scintillator element unit S in the case of FIG. 9) of one gamma-ray detector is selected, and a scintillator element unit (correction target scintillator element unit C in the case of FIG. 9) different from the scintillator element unit of the other gamma-ray detector is selected. When repeating the selection, the time lag histogram concerning the scintillator element units of gamma-ray detectors selected in the past is made a reference, and based on this reference, the time lag histogram concerning the scintillator element units of two gamma-ray detectors selected this time is corrected. And an operation to make the time lag histogram concerning the two corrected scintillator element units of the gamma-ray detectors a new reference is repeated. Since correction is carried out for each scintillator element unit in this way, accuracy can be improved further, compared with carrying out correction for each detector unit as in foregoing Embodiment 1.

[Embodiment 3]

Figure 10:
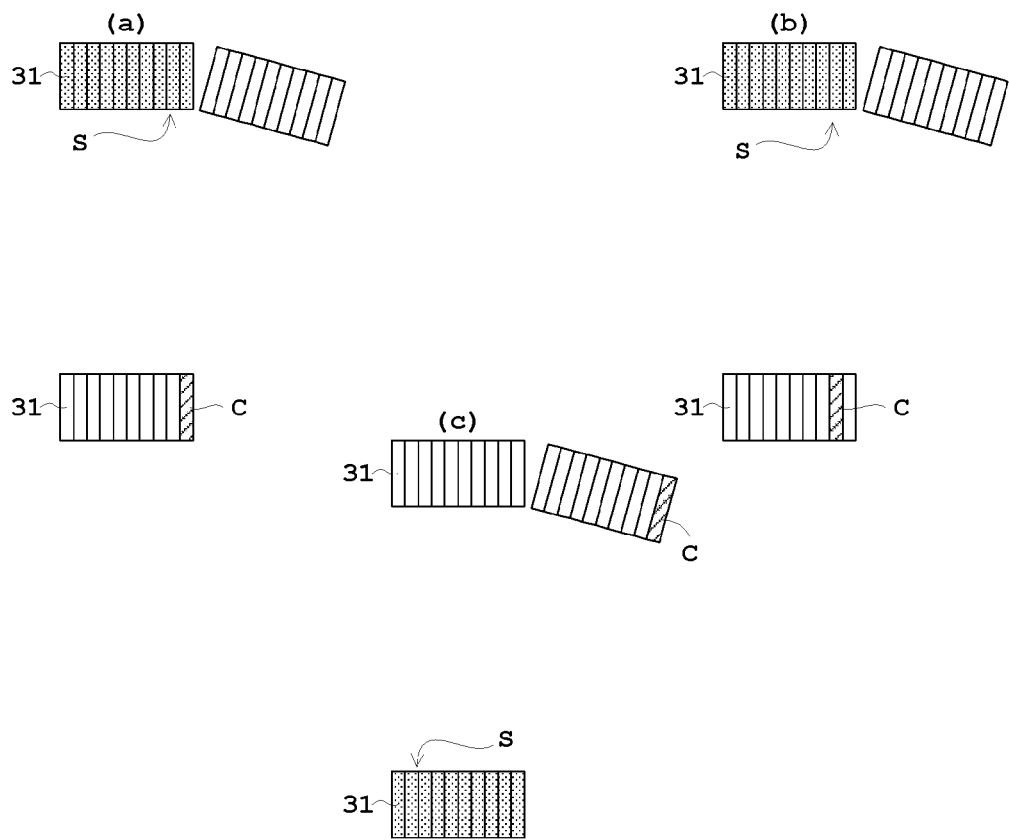
FIGS. 10 (*a*)-(*c*) are front views showing one embodiment of switching between reference scintillator element group and correction target scintillator element unit.

Next, Embodiment 3 of this invention will be described with reference to the drawings. FIG. 10 is a front view showing one embodiment of switching between reference scintillator element group and correction target scintillator element unit. The PET apparatus according to this Embodiment 3, including also Embodiment 4 described hereinafter, is the block diagram shown in FIG. 1. Components common to Embodiments 1 and 2 described hereinbefore will be affixed with the same reference signs, and their description will be omitted.

In Embodiment 1 described hereinbefore, correction is carried out for each scintillator element group (that is, in units of the detector) consisting of a plurality of scintillator elements (scintillator blocks 31). In this Embodiment 3, as in Embodiment 2 described hereinbefore, correction is carried out for each unit of scintillator element consisting of one scintillator element as described below, thereby to improve accuracy. FIG. 10 shows, as does FIG. 9 of Embodiment 2, only the scintillator blocks 31, and the other components (light guides 32 and PMTs 33) are excluded from the illustration.

A reference scintillator element group and a correction target scintillator element unit of gamma-ray detectors which count coincidences are set, respectively. As shown in FIG. 10 (a), a plurality of scintillator blocks 31 of a certain gamma-ray detector are set as reference, and the plurality of scintillator blocks 31 set as reference are regarded as a reference scintillator element group S. One scintillator block 31 of a gamma-ray detector different from the reference scintillator element group S is set as correction target, and the one scintillator block 31 set as correction target is regarded as a correction target scintillator element unit C. Since the specific timing correction is the same technique excepting that a change is made from the detector unit in Embodiment 1 to the scintillator element unit in Embodiment 3, its description is omitted.

As shown in FIG. 10 (b), the reference scintillator element group S selected before is used as reference until the calculation of amounts of correction of all scintillator element units is completed for the gamma-ray detector to which the correction target scintillator element unit C belongs. A scintillator block 31 different from the reference scintillator element unit C shown in FIG. 10 (a) is set as correction target, and the one scintillator block 31 set as correction target is regarded as a correction target scintillator element unit C.

When the calculation of amounts of correction of all scintillator element units is completed for the gamma-ray detector to which the correction target scintillator element unit C belongs, the total number of corrected correction target scintillator element units C is bundled together to be a new reference which, as shown in FIG. 10 (c), is regarded as reference scintillator element group S. One scintillator block 31 of a gamma-ray detector different from the reference scintillator element unit S (in FIG. 9, a gamma-ray detector adjoining the gamma-ray detector of the reference scintillator element unit S in FIG. 9 (a) and FIG. 9 (b)) is set as correction target, and the one scintillator block 31 set as correction target is regarded as a correction target scintillator element unit C. In this way, timing correction is carried out similarly for scintillator element units of the other detectors.

According to the PET apparatus and the timing correction method in this Embodiment 3 having the above construction, of target gamma-ray detectors which count coincidences, a scintillator element group (reference scintillator element group S in the case of FIG. 10) of one gamma-ray detector and a scintillator element unit (correction target scintillator element unit C in the case of FIG. 10) of the other gamma-ray detector are selected. From the selected scintillator element group and scintillator element unit, the scintillator element group is selected, and a scintillator element unit is selected which is different from the scintillator element unit of the other gamma-ray detector. When repeating the selection, the time lag histogram concerning the scintillator element group and scintillator element selected in the past is made a reference, and based on this reference, the time lag histogram concerning the scintillator element group and scintillator element unit selected this time is corrected. And an operation to make the time lag histogram concerning the scintillator element group and scintillator element unit a new reference is repeated. Since correction is carried out for each scintillator element group and scintillator element unit in this way, accuracy can be improved further, compared with carrying out correction for each detector unit as in foregoing Embodiment 1. Calculation time and the burden can be reduced, compared with carrying out correction for each scintillator element unit as in foregoing Embodiment 2.

[Embodiment 4]

Figure 11:
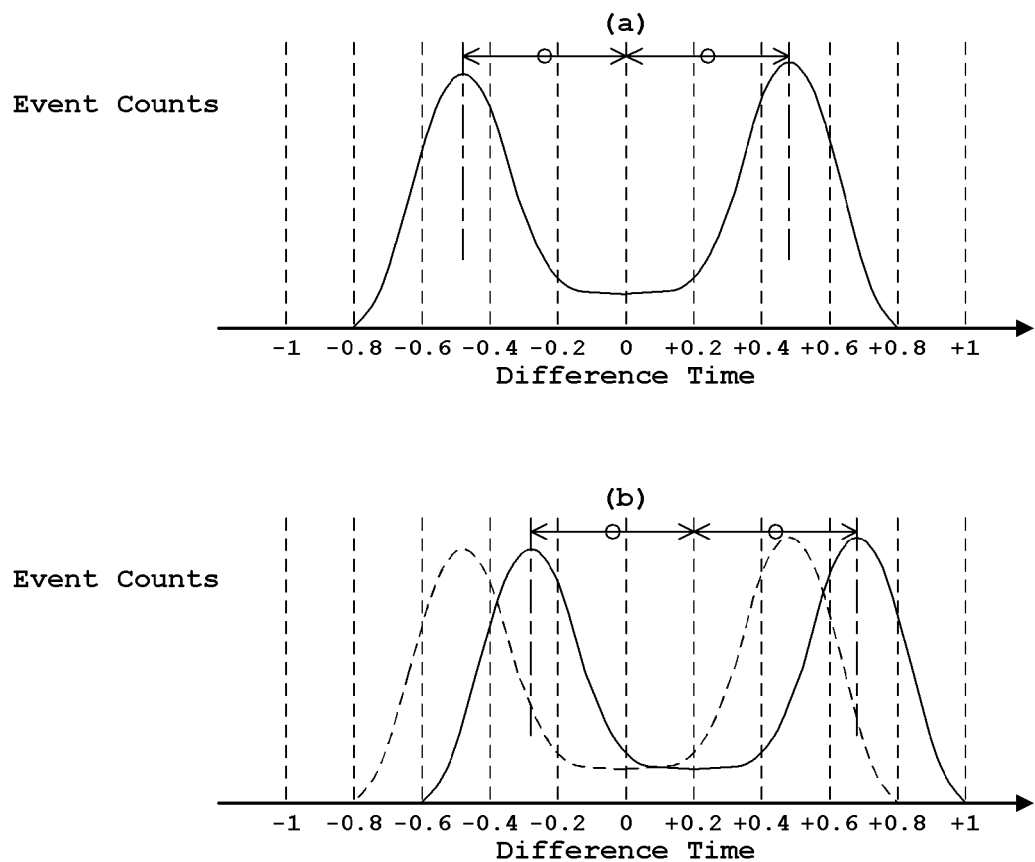
FIGS. 11 (*a*) and (*b*) are explanatory views of time lag histograms at a time of scintillator elements with self-radioactivity.

Next, Embodiment 4 of this invention will be described with reference to the drawings. FIG. 11 is an explanatory view of time lag histograms at a time of scintillator elements with self-radioactivity. The PET apparatus according to this Embodiment 4 is the block diagram shown in FIG. 1. Components common to Embodiments 1-3 described hereinbefore will be affixed with the same reference signs, and their description will be omitted.

In this Embodiment 4, as distinct from Embodiment 1 described hereinbefore, the scintillator blocks are constructed of self-radioactivity (element which releases a plurality of radioactive rays at the same time) represented by Lu-176 or the like, or a substance to which self-radioactivity is added (e.g. LYSO including Lu). That is, the scintillator blocks are scintillator elements with self-radioactivity, and the detectors have the scintillator elements having self-radioactivity. The scintillator blocks may be constructed by applying a thin-film tape consisting of a substance with self-radioactivity added thereto to crystal elements without self-radioactivity (e.g. GSO), or by applying a coating consisting of a substance with self-radioactivity added thereto to crystal elements without self-radioactivity.

The scintillator elements with self-radioactivity include a nuclide that causes $\alpha$ or $\beta$-decay and releases gamma rays accompanying the $\alpha$ or $\beta$-decay. In FIG. 11, time lag histograms are acquired based on the radiation (gamma rays here) from the self-radioactivity.

As shown in FIG. 11, as in FIG. 6 of Embodiment 1 described hereinbefore, the time lag histogram is a count value distribution of time lag variations, in which the horizontal axis represents a difference in time stamp (i.e. time lag) between each pair of detectors 3 (indicated "Difference Time" in FIG. 11), and the vertical axis represents count values (indicated "Event Counts" in FIG. 11).

When the scintillator elements have self-radioactivity, as shown in FIG. 11 (a), the time lag histogram has, appearing thereon, a temporal location where the total count value is the largest and a temporal location where the total count value is the second largest. Therefore, this Embodiment 4 regards, as reference value, a time lag with a middle value between a time lag at which the total count value is the largest and a time lag at which the total count value is the second largest in the time lag histogram made the reference. This reference value is set to "0". The time lag histogram to be corrected has a shift relative to the time lag histogram made the reference, and is shifted sideways as shown in a solid line in FIG. 11 (b). So, a shift amount for returning "0" to the reference value, i.e. the time lag histogram to be corrected from the solid line to a dotted line in FIG. 11 (b), is determined as an amount of correction. Then, the time lag histogram is corrected by applying this amount of correction.

According to the PET apparatus and the timing correction method in this Embodiment 4 having the above construction, a time lag with a middle value between a time lag at which the total count value is the largest and a time lag at which the total count value is the second largest in the time lag histogram made the reference is used as reference value, and the time lags of the time lag histograms are corrected based on the above reference value.

When the detectors have scintillator elements with self-radioactivity as in this Embodiment 4, the timing of radiation from the self-radioactivity of the scintillator element of one detector being detected in the largest amount by the scintillator element of the other detector, and the timing of radiation from the self-radioactivity of the scintillator element of the other detector being detected in the largest amount by the scintillator element of the one detector, are the temporal location where the total count value is the largest, or the temporal location where the total count value is the second largest. This means that the middle value between two time lags corresponding to these timings is a time at which coincidence counting is most likely to occur. Therefore, the times can be uniformed by correcting the time lags of the time lag histograms based on the reference value reflecting that time.

This invention is not limited to the foregoing embodiments, but may be modified as follows:

(1) In each of the foregoing embodiments, the positron CT apparatus (PET apparatus) is the stand-alone type. It is applicable also to a PET-CT apparatus which combines a PET apparatus and a CT apparatus.

(2) Each of the foregoing embodiments has been described taking gamma rays as an example of radiation, but alpha rays or beta rays may be used. Particularly where the detectors have scintillator elements with self-radioactivity as in Embodiment 4, time lag histograms may be used also in detecting alpha rays or beta rays with the detectors themselves of the scintillator elements having caused alpha or beta-decays.

(3) Each of the foregoing embodiments is directed to DOI detectors. However, this invention is applicable also to detectors which do not discriminate the depth direction. This invention is applicable to detectors constructed to include a single scintillator element.

(4) Each of the foregoing embodiments is applied to the detectors arranged in a ring form. However, this invention is applicable also where a plurality of detectors are provided simply instead of being installed in the ring form.

The invention claimed is:

1. A positron CT apparatus having a plurality of detectors for detecting radiation released from a positron-emitting radioactive drug given to a patient, comprising:
   a computing device, in connection with a time lag histogram showing a count value distribution of time lag variations for each pair of detectors which count coincidences of the radiation, for:
   (i) selecting a first detector as a reference detector and a second detectors as a count detector which count coincidences, to obtain a time lag histogram of the first detector and the second detector, and selecting a group of detectors including the second detector,
   (ii) selecting a detector different from the second detector from the group of detectors,
   (iii) correcting a time lag histogram of the first detector and the selected different detector using the time lag histogram of the first detector and the second detector,
   (iv) newly selecting a detector, which has not been previously selected, from the group of detectors, and correcting a time lag histogram of the first detector and the newly selected detector using the time lag histogram of the first detector and the second detector,
   (v) repeating (iv) until all of the detectors in the group of detectors are subjected to (iv), and
   repeating (i)-(v) by selecting a new reference detector, a new counter detector and a new group of detectors until all of the plurality of detectors in the positron CT apparatus are subjected to the selection and correction, the new reference detector being selected from a previously selected group of detectors; and
   a coincidence counting circuit for counting coincidences of the radiation based on the time lag histogram for each pair of detectors repeatedly corrected by the computing device.

2. The positron CT apparatus according to claim 1, wherein:
   a time lag at which a total count value in the time lag histogram made the reference becomes the largest is used as reference value; and
   the computing device corrects time lags of the time lag histograms based on the reference value.

3. The positron CT apparatus according to claim 1, wherein:
   a time lag with a middle value between a time lag at which a total count value is the largest and a time lag at which the total count value is the second largest in the time lag histogram made the reference is used as reference value; and
   the computing device corrects time lags of the time lag histograms based on the reference value.

4. The positron CT apparatus according to claim 1, wherein:
   the detector includes:
   a plurality of scintillator elements which produce fluorescence upon incidence of the radiation; and
   a photoelectric conversion device which detects the radiation by carrying out photoelectric conversion of light from each scintillator element; and
   the detectors are DOI detectors constructed by stacking the respective scintillator elements in a depth direction of the radiation.

5. The positron CT apparatus according to claim 1, comprising an external radiation source which emits radiation corresponding in type to the radioactive drug, or a phantom which emits, from inside, radiation corresponding in type to the radioactive drug, the time lag histograms being acquired based on the radiation from the external radiation source or the phantom.

6. The positron CT apparatus according to claim 1, wherein the detectors have scintillator elements with self-radioactivity, the time lag histograms being acquired based on radiation from the self-radioactivity.

7. A positron CT apparatus having a plurality of detectors for detecting radiation released from a positron-emitting radioactive drug given to a patient, comprising:
  a computing device, in connection with a time lag histogram showing a count value distribution of time lag variations for each pair of detectors which count coincidences of the radiation, for selecting two target detectors which count coincidences, selecting one detector out of the two selected detectors, selecting a detector different from the other detector, and when repeating the selection, making a time lag histogram concerning two detectors selected in the past a reference, correcting a time lag histogram concerning detectors selected this time based on the reference, and repeating an operation to make the corrected time lag histogram concerning the two detectors a new reference; and
  a coincidence counting circuit for counting coincidences of the radiation based on the time lag histogram for each pair of detectors repeatedly corrected by the computing device, wherein:
  a time lag with a middle value between a time lag at which a total count value is the largest and a time lag at which the total count value is the second largest in the time lag histogram made the reference is used as reference value, and
  the computing device corrects time lags of the time lag histograms based on the reference value.

8. The positron CT apparatus according to claim 1, wherein the new reference detector is located at an end of the previously selected group of detectors.

* * * * *